(12) United States Patent
Brudeniuc

(10) Patent No.: US 6,562,972 B1
(45) Date of Patent: May 13, 2003

(54) METHOD FOR PREPARING HETEROCYCLIC-CARBOXYLIC ACIDS

(75) Inventor: Juan Jesus Brudeniuc, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/908,997

(22) Filed: Jul. 19, 2001

(51) Int. Cl.$^7$ ............................................. C07D 241/42
(52) U.S. Cl. ...................... 544/353; 546/108; 546/170; 548/261; 548/306.4
(58) Field of Search ......................................... 544/353

(56) References Cited

U.S. PATENT DOCUMENTS

| | | | | |
|---|---|---|---|---|
| 3,772,273 A | 11/1973 | Gilbert | ........................ | 260/250 |
| 3,960,963 A | 6/1976 | Gavin | | |
| 5,380,719 A | 1/1995 | Kim | ............................ | 514/85 |
| 5,747,492 A | * 5/1998 | Lynch et al. | | |

FOREIGN PATENT DOCUMENTS

| | | | |
|---|---|---|---|
| DE | 4410418 | | 9/1995 |
| EP | 0257518 | | 3/1988 |
| WO | 00/51608 | * | 9/2000 |

OTHER PUBLICATIONS

R. Granger, S. Deadwyler, et al. "Facilitation of Glutamate Receptors Reverses an Age–Associated Memory Impairment in Rats" Synapse, 22, pp. 332–337, 1996.
G. Lynch, M. Kessler, et al., "Psychological Effects of a Drug that Facilitates Brain AMPA Receptors", International Clinical Psychopharmacology, 11, pp. 13–19, 1996.
W. F. Gum, "Structure vs. Reactivity in Quinoxalinecarboxylic Acids and Esters", J. Org. Chem. 30, 3982, 1965.
H. Huang, A. R. Lee, C. I. Lin, et al., Yixue Yanjiu, 13, 247–54, 1993.
B. Shilling, Ber., 34, pp 902–907, 1901.
A. Tallec, Ann. Chim. (Paris), 3, 164, 1968 (Abstract for).
V. Cere, D. Dal Monte, E. Sardi, Tetrahedron, 28, 3271, 1972.
M. Hudlicky, "Oxidations in Organic Chemistry", ACS Monograph 186, 1990.
R. A. Sheldon, J. K. Kochi, "Metal–Catalyzed Oxidation of Organic Compounds", Chapter 5, pp. 121–151, Academic Press, 1981.
2–3–Pyrazinedicarboxylic acid: "Organic Synthesis" Coll. vol. 4, pp. 824–827, J. Wiley & Sons, Inc., NY 1963.
R. A. Sheldon, J. K. Kochi, "Metal Catalyzed Oxidation of Organic Compounds", Chapter 7, pp. 189–214, Academic Press, 1981.
J. C. Cavagnol, F. Y. Wiselogle, J. Am. Chem. Soc., 69, 795, 1947.
Thomas D. Waugh, NBS: N–Bromosuccinimide Its Reactions and Uses; Araphoe Chemicals, Inc. Boulder Co. 1951.
Benzoyl Piperadine: "Organic Synthesis", Coll. vol. 1 pp. 108–110, J. Wiley & Sons, Inc. New York, 1943.
European Search Report, 02015662.6–2101, dated Oct. 31, 2002.
R. Oi, et al., "Selective Conversion of m–Hydroxybenzyl Alcohol to m–Hydroxybenzaldehyde," Chemistry Letters (1998), pp. 1115–1116.
A. R. Prasad, et al., "Vapor phase oxidation of 4—pyridine methanol to 4—pyridine carboxaldehyde", Synth. Commun., vol. 20, No. 21 (1990), pp. 3385–3390.

* cited by examiner

Primary Examiner—Emily Bernhardt
(74) Attorney, Agent, or Firm—Michael Leach

(57) ABSTRACT

The present invention relates to a method for preparing quinoxaline-5- and 6-carboxylic acids. The method comprises contacting an aqueous alkaline suspension of a 5- or 6-halomethyl quinoxaline with oxygen in the presence of a transition metal catalyst, to form the respective quinoxaline-5- or 6-carboxylic acid. The method for oxidizing benzylic methyl groups may also be employed to prepare a wide variety of heterocyclic carboxylic acid compounds.

6 Claims, No Drawings

METHOD FOR PREPARING HETEROCYCLIC-CARBOXYLIC ACIDS

BACKGROUND OF THE INVENTION

The present invention relates to a method for preparing heterocyclic carboxylic acid compounds, especially quinoxaline-5- and 6-carboxylic acids.

The disclosures referred to herein to illustrate the background of the invention and to provide additional detail with respect to its practice are incorporated herein by reference and, for convenience; are numerically referenced in the following text and respectively grouped in the appended bibliography.

Quinoxaline-6-carboxylic acid is an important chemical intermediate for the preparation of compounds such as AMPHAKINE CX516® [1-(quinoxalin-6-ylcarbonyl)piperidine], a drug being tested for the treatment of Alzheimer's disease, Attention Deficit Hyperactivity Disorder (ADHD), Mild Cognitive Impairment (MCI), Chronic Schizophrenia and male sexual dysfunction (1). The preparation of AMPHAKINE CX516® involves the conversion of 3,4-diaminobenzoic acid to quinoxaline-6-carboxylic acid with sodium glyoxal bisulfite, followed by amidation of the resulting acid with piperidine, as set out below (2, 12).

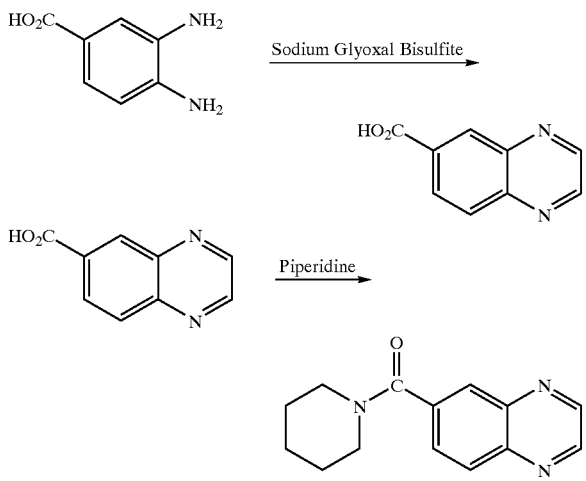

Although the preparation of AMPHAKINE CX516® appears straightforward, the synthesis requires the use of 3,4-diaminobenzoic acid, an expensive starting material. For example, preparation of the isomeric 2,3-diaminobenzoic acid employs a multi-step method that includes oxidation, reduction, amidation, nitration, separation of isomers, further reduction, and hydrolysis, as set out below (3). Preparation of the isomeric 3,4-diaminobenzoic acid can be carried out using this multi-step method by isolating and further reacting the 3-amido, 4-nitrobenzoic acid isomer.

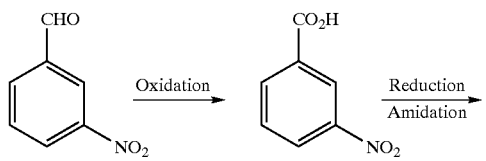

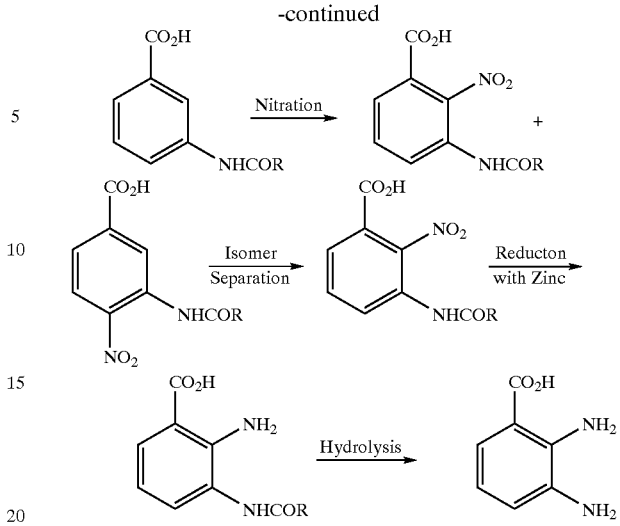

Other methods for preparing 3,4-diaminobenzoic-acid involve the electrochemical reduction of 3,4-dinitrobenzoic acid and the hydrogenation of substituted benzofurazans (4). These methods also employ expensive chemical intermediates.

Initial attempts by the applicant to prepare quinoxaline-6-carboxylic acid focused on a one step selective oxidation of the benzyl group to a carboxylic acid without affecting the aromatic rings, as set out below.

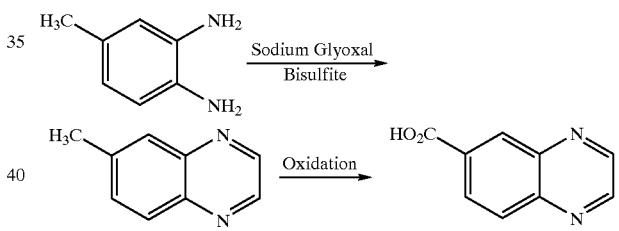

Many methods are known for the direct oxidation of benzylic methyl groups to carboxylic acids. These methods typically employ a strong oxidizing agent, such as potassium permanganate, that reacts with a methyl group providing the remainder of the molecule is not reactive to the oxidizing agent (5). Thus, toluene can be oxidized with potassium permanganate to benzoic acid without affecting the benzene ring (5). Catalytic methods are generally more acceptable for industrial scale because theses methods employ milder oxidizing agents, i.e., air or oxygen, to carry out the oxidation of benzylic methyl groups to the corresponding carboxylic acid (6). The oxidation of 5- and 6-methyl-quinoxalines to 5- and 6-quinoxaline-carboxylic acids is not so straightforward, however, because strong oxidizing agents, such as potassium permanganate, degrade the aromatic ring yielding 2,3-pyrazinedicarboxylic acid (7):

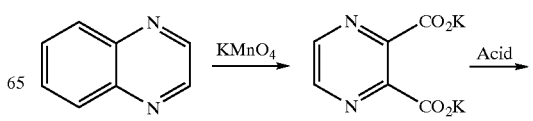

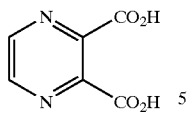

Milder oxidizing agents, i.e., air or oxygen in the presence of a catalyst, on the other hand, have no effect on the benzylic methyl group of 5- or 6-methyl-quinoxaline. Air in the presence of a cobalt salt can oxidize toluene to benzoic acid (6) but does not oxidize methyl-quinoxaline to quinoxaline-carboxylic acid. Similarly, air and oxygen in the presence of a palladium or platinum catalyst are also ineffective (8). Most known oxidizing reagents are either too mild to react with methyl-quinoxalines or are too reactive causing structural changes.

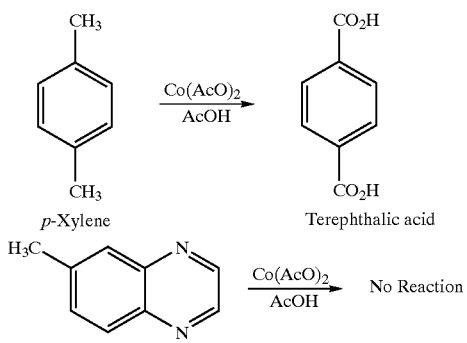

Because attempts to prepare quinoxaline-6-carboxylic acid via a one-step selective oxidation of the benzyl group were not successful, a two-step method to prepare quinoxaline-6-carboxylic acid was developed. In the first step, 6-methyl-quinoxaline is halogenated to provide a 6-halomethyl-quinoxaline intermediate. In the second step, the 6-halomethyl-quinoxaline intermediate is oxidized to the corresponding quinoxaline-6-carboxylic acid.

BRIEF SUMMARY OF THE INVENTION

The present invention pertains to a method for preparing quinoxaline-5- and 6-carboxylic acids (I) which comprises contacting an aqueous alkaline suspension of a 5- or 6-halomethyl quinoxaline (II) with oxygen in the presence of a transition metal catalyst, to form the respective quinoxaline-5- or 6-carboxylic acid (I), wherein X is halogen.

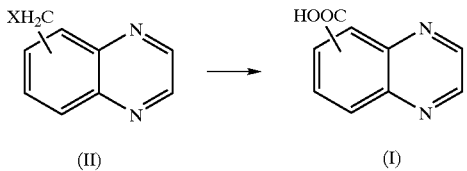

The present invention also pertains to a method for preparing a carboxylic acid selected from the group consisting of:

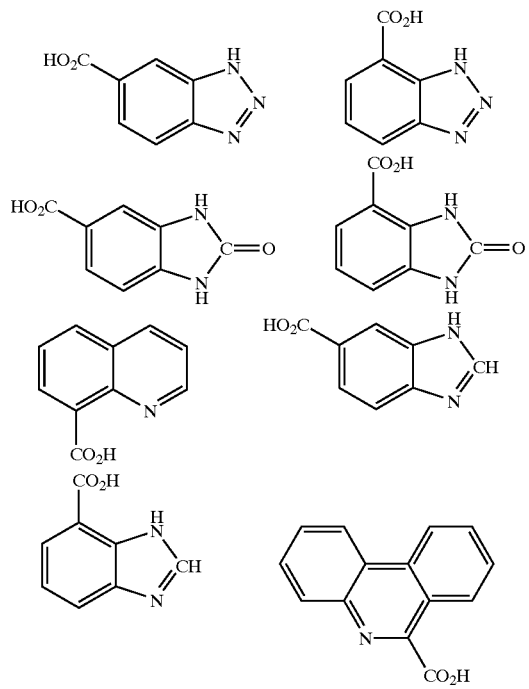

The method comprises contacting an aqueous alkaline suspension of a halomethyl precursor compound of the respective carboxylic acid with oxygen in the presence of a transition metal catalyst, to form the respective carboxylic acid.

DETAILED DESCRIPTION OF THE INVENTION

The present invention pertains to a two-step method for converting benzyl heterocyclic compounds to the corresponding carboxylic acid heterocyclic compounds. The two-step method is especially suitable for converting 5- and 6-benzyl quinoxalines to the corresponding quinoxaline-5- and 6-carboxylic acids. The 5- and 6-benzyl quinoxalines may be prepared from ortho-diaminotoluenes, such as 2,3- and 3,4-diaminotoluene, by condensation with sodium glyoxal bisulfite. The method for oxidizing benzylic methyl groups may also be employed to prepare a wide variety of heterocyclic carboxylic acid compounds.

In the first step, 6-methyl-quinoxaline is halogenated to provide a 6-halomethyl-quinoxaline intermediate.

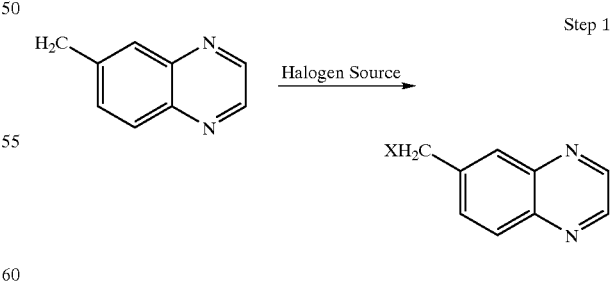

Step 1

This first step is more fully described in copending patent application Ser. No. 09/909,000, now U.S. Pat. No. 6,492,517, entitled "Method For Preparing Halomethyl Heterocyclic Compounds" filed by applicant on Jul. 19, 2001 concurrently with the present patent application, and assigned to the assignee of this application, which is hereby incorporated by reference.

In the second step, the 6-halomethyl-quinoxaline intermediate is oxidized to the corresponding quinoxaline-6-carboxylic acid.

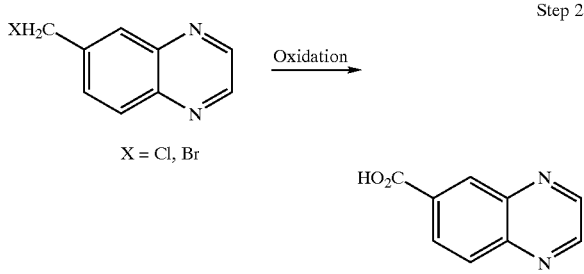

As set out above, 5- and 6-benzyl quinoxalines may be prepared from ortho-diaminotoluenes, such as 2,3- and 3,4-diaminotoluene, by condensation with sodium glyoxal bisulfite. For example, 6-benzyl quinoxaline may be prepared by condensation of 3,4-diaminotoluene with sodium glyoxal bisulfite (9).

Because attempts to prepare quinoxaline-6-carboxylic acid via a one-step selective oxidation of the benzyl group were not successful, a two-step method to prepare quinoxaline-6-carboxylic acid was developed. In the first step, 6-methyl-quinoxaline is halogenated to provide a 6-halomethyl-quinoxaline intermediate. In the second step, the 6-halomethyl-quinoxaline intermediate is oxidized to the corresponding quinoxaline-6-carboxylic acid.

In the first step of the synthesis, a benzylic methyl heterocyclic compound and a halogenating agent, such as N-chlorosuccinimide (NCS) or N-bromosuccinimide (NBS), are reacted in the presence of a radical initiator, such as benzoyl peroxide or azobisisobutyronitrile, in a suitable solvent, to form the respective halomethyl heterocyclic compound, such as 5- or 6-halomethyl quinoxaline (I). Suitable solvents may be selected from the group consisting of fluorobenzene, difluorobenzenes, trifluorobenzenes, chlorobenzene, dichlorobenzenes, trichlorobenzenes, α,α,α-trifluorotoluene and α,α,α-trichlorotoluene.

The method for halogenating benzylic positions may also be employed to halogenate a variety of heterocyclic compounds. The method typically affords good yields of halomethyl-quinoxalines when [6QX]/[benzoyl peroxide] ≦40 while maintaining a temperature in the range of 60° C. to 115° C. for a period of 1 to 12 hours. Yields for benzylic brominations (conversions ≧95%, selectivities ≧97%) are in general better than for benzylic chlorinations (conversions 60%, selectivities ~75–80%). The 5- or 6-halomethyl quinoxaline may be a 5-halomethyl quinoxaline or may be a 6-halomethyl quinoxaline. The halomethyl may be a chloromethyl or may be a bromomethyl.

The method comprises contacting the benzyl precursor compound of the respective halomethyl compound with a halogenating agent in the presence of a radical initiator in a solvent selected from the group consisting of fluorobenzene, difluorobenzenes, trifluorobenzenes, chlorobenzene, dichlorobenzenes, trichlorobenzenes, α,α,α-trifluorotoluene and α,α,α-trichlorotoluene, to form the respective halomethyl compound.

The benzylic halogenation of heterocyclic compounds, such as methyl-quinoxalines, depends on a variety of factors including the halogenating agent, the radical initiator, the solvent, temperature, reaction time, reagent concentrations, and procedure.

The halogenating agents which may be employed in the present invention may be any halogenating agent which is capable of selectively halogenating the benzylic methyl group of a heterocyclic compound. The term "halogen", as used herein, refers to the elements fluorine, chlorine, bromine, and iodine. Preferred halogens are chlorine and bromine. Non-limiting illustrative halogenating agents may be selected from the group consisting of N-chlorosuccinimide, N-bromosuccinimide, $Cl_2$, $Br_2$, t-butyl hypochlorite, N-chloroglutarimide, N-bromoglytarimide, N-chloro-N-cyclohexyl-benzenesulfonimide, and N-bromophthalimide. Preferred halogenating agents are N-chlorosuccinimide and N-bromosuccinimide.

The radical initiators which may be employed in the present invention may be any radical initiator which is capable of catalyzing the halogenating agent to selectively halogenate the benzylic methyl group of a heterocyclic compound. The presence of an initiator is essential for the reaction to occur because radicals propagate these reactions. Non-limiting illustrative radical initiator agents may be selected from the group consisting of benzoyl peroxide, azobisisobutyronitrile (AIBN), and diacyl peroxides, dialkyl peroxydicarbonates, and tert-alkylperoxyesters, monoperoxycarbonates, di(tert-alkylperoxy)ketals, ketone peroxides. Preferred radical initiators are benzoyl peroxide and azobisisobutyronitrile. Alternatively, radicals can be generated photochemically.

The solvents which may be employed in the present invention may be any solvent which is capable of promoting the halogenating agent to selectively halogenate the benzylic methyl group of a heterocyclic compound. The choice of solvent is critical. The solvent must (a) be a media in which the halogenating agent has a low, but definite, solubility; (b) be stable to the halogenating agent allowing the halogenating agent to react preferentially at the methyl group of the heterocyclic compound to provide a halomethyl-heterocyclic compound that is stable in the solvent under the reaction conditions; and (c) be environmentally acceptable. Most conventional benzylic bromination procedures employ highly toxic solvents which are rigorously restricted on an industrial level. Suitable solvents may be selected from the group consisting of fluorobenzene, difluorobenzenes, trifluorobenzenes, chlorobenzene, dichlorobenzenes, trichlorobenzenes, α,α,α-trifluorotoluene and α,α,α-trichlorotoluene. Preferred solvents are chlorobenzene and α,α,α-trifluorotoluene.

In the second step of the synthesis, an aqueous alkaline suspension of a 5- or 6-halomethyl quinoxaline (II) is contacted with oxygen in the presence of a transition metal catalyst, to form the respective quinoxaline-5- or 6-carboxylic acid (I). X is halogen.

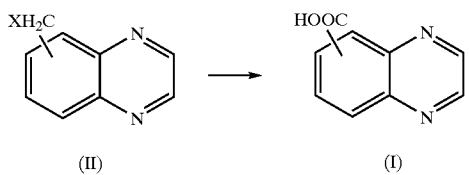

The method for oxidizing benzylic methyl groups may also be employed to prepare a wide variety of heterocyclic carboxylic acid compounds.

In one preferred embodiment, the invention is directed to a method for preparing quinoxaline-5- and 6-carboxylic acids (I). The method comprises contacting an aqueous alkaline suspension of a 5- or 6-halomethyl quinoxaline (II) with oxygen in the presence of a transition metal catalyst, to form the respective quinoxaline-5- or 6-carboxylic acid (I). X is halogen.

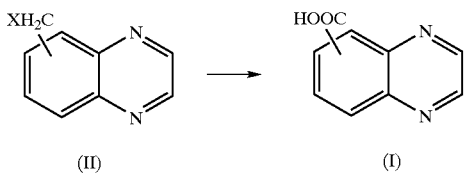

In another preferred embodiment, the invention is directed to a method for preparing a carboxylic acid selected from the group consisting of:

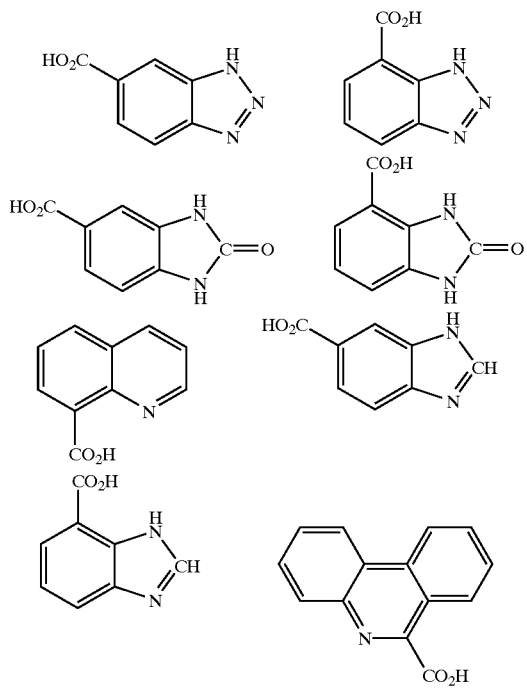

The method comprises contacting an aqueous alkaline suspension of a halomethyl precursor compound of the respective carboxylic acid with oxygen in the presence of a transition metal catalyst, to form the respective carboxylic acid.

The method for oxidizing benzylic halomethyl compounds, such as halomethyl-quinoxalines, depends on a variety of factors including the aqueous alkaline suspension, the source of oxygen, the transition metal catalyst, temperature, reaction time, reagent concentrations, and procedure.

The aqueous alkaline suspension which may be employed in the present invention may be any aqueous alkaline suspension of a 5- or 6-halomethyl quinoxaline (II) having a pH value which is capable of selectively oxidizing the benzylic halomethyl group of a heterocyclic compound. Preferably, the aqueous alkaline suspension of a 5- or 6-halomethyl quinoxaline (II) may have a pH value in the range from about 7 to about 14, preferably from about 8 to about 14, and more preferably from about 12 to about 14. Suitable sources for providing the alkalinity include alkali and alkaline earth metal oxides, hydroxides, carbonates, and tetraalkylammonium hydroxide salts.

The source of oxygen which may be employed in the present invention may be any source of oxygen which is capable of selectively oxidizing the benzylic halomethyl group of a heterocyclic compound. Oxygen, air, and mixtures thereof may be employed.

The transition metal catalysts which may be employed in the present invention may be any catalyst which is capable of selectively catalyzing the oxidation of the benzylic halomethyl group of a heterocyclic compound. Non-limiting illustrative transition metal catalysts may be selected from the group consisting of Pd, Pt, Ru, Co, Mn, Cu, and V, especially on supports such as carbon, alumina, silica, and titania. Preferably, the transition metal catalyst is Pd/C or Pt/C.

The temperatures which may be employed in the method for preparing quinoxaline-5- and 6-carboxylic acids of the present invention are important to ensure that the benzylic group is oxidized. The temperature should be chosen so that an optimum reaction rate can be reached. Such temperatures may range from about 50° C. to about 150° C., preferably from about 80° C. to about 120° C.

The reaction times which may be employed in the present invention play an important role in the method for preparing quinoxaline-5- and 6-carboxylic acids. Thus, reaction times should be optimum to ensure maximum conversion. Suitable reaction times may range from about 4 to about 72 hours, preferably from about 8 to about 48 hours.

The reagent concentrations which may be employed in the present invention should be optimum to ensure maximum conversion. The quinoxaline concentrations may range from about 0.05M to about 0.5M, preferably from about 0.1M to about 0.3M. The alkali concentration may range from about 0.5M to about 3M, preferably from about 0.9M to about 1.5M.

The method of the present invention has been used for the synthesis of quinoxaline-6-carboxylic acid, a precursor for AMPHAKINE CX516® (I), but other carboxylic acids may also be prepared by the methods of the present invention. In particular, substrates that are fragile towards strong oxidants but are impervious towards mild oxidizing agents (i.e. quinolines, triazoles, ureas derived from ortho-diaminotoluenes, etc) can be oxidized to their corresponding acids. Examples of carboxylic acids that can be made by the present method are:

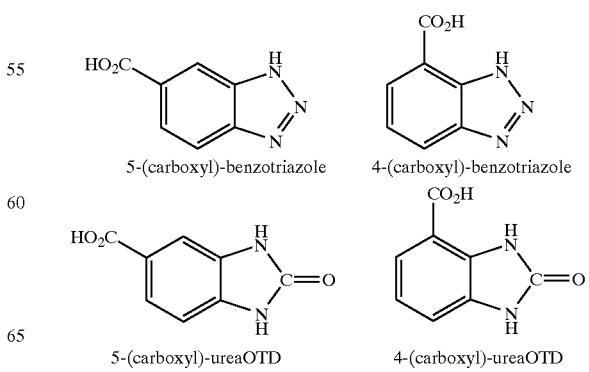

5-(carboxyl)-benzotriazole    4-(carboxyl)-benzotriazole 5-(carboxyl)-ureaOTD    4-(carboxyl)-ureaOTD -continued

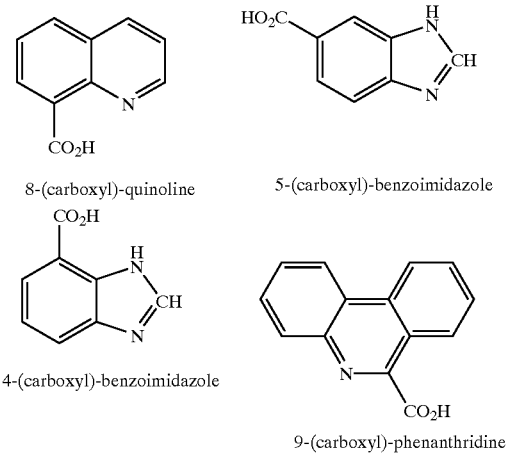

8-(carboxyl)-quinoline 5-(carboxyl)-benzoimidazole 4-(carboxyl)-benzoimidazole 9-(carboxyl)-phenanthridine After oxidation of the halomethyl-quinoxaline, the product can remain in the aqueous solution as a salt of the quinoxaline-carboxylic acid (i.e., sodium 6-quinoxaline carboxylate). The resulting aqueous solution can then be extracted if necessary with ether (to remove any remaining organic contaminant) followed by acidification with a mineral acid. The pale yellow solid that precipitates (i.e. 6-quinoxaline carboxylic acid) can be filtered, washed with water, and air-dried (~80% yield). The typical yield for the first step (halomethyl-quinoxaline synthesis) is 97% selectivity and 95% conversion. The typical yield for the second step (oxidation step) is ~80%.

All attempts by applicant to prepare quinoxaline-6-carboxylic acid directly from 6-methyl-quinoxaline failed (i.e., without making the halomethyl-quinoxaline intermediate). These attempts included air oxidation with cobalt catalyst in acetic acid; air oxidation with Co/Mn/Cl—/Br⁻ catalyst in acetic acid; air oxidation with 5% Pd/C catalyst; $KMnO_4$; $KCrO_4$; and ruthenium catalyst in the presence of sodium hypochlorite.

There are several advantages in using the present method compared to conventional methods. The present method is simple because the new method can convert a readily available chemical (2,3- or 3,4-diaminotoluene) into a valuable pharmaceutical intermediate in only three steps. Also, the method requires only routine operations (filtrations, distillation, extraction, etc) without the need to employ complex chemical operations or purification procedures. The present method is also economical because the method does not use exotic chemicals and it can produce the desire product in a good yield. Also, using catalytic air oxidation creates fewer environmental problems typically associated with oxidation procedures that rely on metal-oxo compounds (i.e., potassium permanganate). Because the new method takes advantage of diaminotoluenes as a raw material, the synthesis of 6-quinoxaline-carboxylic acid is less laborious and more economical.

Throughout this disclosure, applicant will suggest various theories or mechanisms by which applicant believes the present methods function. While applicant may offer various mechanisms to explain the present invention, applicant does not wish to be bound by theory. These theories are suggested to better understand the present invention but are not intended to limit the effective scope of the claims.

The present invention is further illustrated by the following examples which are presented for purposes of demonstrating, but not limiting, the preparation of the compounds and compositions of this invention.

EXAMPLE

Example 1

Synthesis of 6-chloromethyl-quinoxaline

In a 500 ml flask, 6-methyl-quinoxaline (10 g, 69.4 mmol) was dissolved together with N-chlorosuccinimide (14 g, 105.3 mmol) and benzoyl peroxide (BP, 0.4 g, 1.65 mmol) in 240 g of acetonitrile. The flask was connected to a reflux-condenser and the solution was refluxed for 6 hours followed by another addition of 0.1 g of benzoyl peroxide. Reflux was then continued for another 6 hours.

| Solvent | [6QX] | [NCS] | [BP]$_{final}$ | [NCS]/[6QX] | [6QX]/[BP]$_{final}$ |
|---|---|---|---|---|---|
| Acetonitrile | 0.22 | 0.34 | 6.7 × 10⁻³ | 1.5 | 33 |

The samples were then analyzed by GC and Mass spectroscopy to show the following compounds:

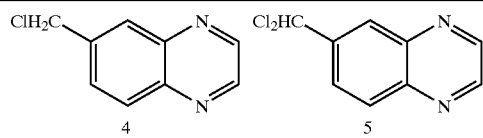

|  | Total Reaction Time = 6 hrs | | Total Reaction Time = 12 hrs | |
|---|---|---|---|---|
| Product | % Selectivity | % Conversion | % Selectivity | % Conversion |
| 4 | 77.0 | 40.0 | 79.7 | 60 |
| 5 | 3.5 | 1.8 | 5.8 | 4.4 |
| Unknowns | 19.5 | 10.0 | 14.5 | 11.0 |

The acetonitrile solution was concentrated by vacuum distillation to give a yellow suspension that was extracted with pentane (10 times, 50 ml each). The pentane extracts contained all the quinoxaline products while the residue was composed mainly of succinimide and unreacted N-chlorosuccinimide. The pentane extracts were vacuum dried to give 9.2 g of a yellow solid. GC-MS analysis showed that 80% of the extracted yellow solid was composed of 6-chloromethyl-quinoxaline ($M^+$=178) while the remaining 20% corresponded mainly to unreacted 6-methyl-quinoxaline. The chloro-compound was analyzed by $^1H$ NMR showing the following resonances: $^1HNMR$ ($CDCl_3$): 4.69 ppm (—$CH_2Cl$), 7.97 ppm (singlet, 1 H), 7.68 ppm (1 H, doublet, J=10 Hz), 7.98 (1 H, doublet, J=10 Hz), 8.73 (2H, broad doublet). These analyses confirmed the structure of the desired compound.

Example 2

Synthesis of 6-bromomethyl-quinoxaline

In a 100 ml flask, 6-methyl-quinoxaline (2.5 g, 17.4 mmol) was dissolved together with N-bromosuccinimide (3.4 g, 19 mmol) and benzoyl peroxide (0.2 g, 0.82 mmol) in 70 g of 1,2-dichloroethane. The concentration of the reactants and some of their molar ratios is shown below:

| Solvent | [6QX] | [NBS] | [BP]  | [NBS]/[6QX] | [6QX]/[BP] |
|---------|-------|-------|-------|-------------|------------|
| 1,2-DCE | 0.31  | 0.35  | 0.015 | 1.1         | 20         |

The reaction mixture was refluxed for 30 minutes (bp. 83° C.) followed by an addition of benzoyl peroxide (0.05 g dissolved in 2 ml of $C_2H_4Cl_2$). This mixture was refluxed for an additional 30 minutes followed by a second addition of benzoyl peroxide (0.05 g dissolved in 2 ml of $C_2H_4Cl_2$). The mixture was refluxed for an additional 100 minutes and the reaction was stopped.

After all benzoyl peroxide was added, samples were analyzed and the results are shown in the table below:

| | Total Reaction Time = 140 min | |
|---|---|---|
| Product | % Selectivity | % Conversion |
| 1 | 92.0 | 68.0 |
| 2 | 5.0  | 3.6  |
| 3 | 3.0  | 2.0  |

The dark reddish solution obtained was evaporated under vacuum to give an orange-reddish residue that was extracted with pentane. This glue-like residue is very difficult to extract with pentane but if 1 or 2 ml of acetonitrile is added, all the solid residue forms a liquid suspension that can be easily extracted with pentane under vigorous stirring. The suspension was extracted with pentane (~10 times, 20 ml each) until all product was extracted. All other by-products such as NHS or unreacted NBS remained in the acetonitrile suspension. Using this procedure 2.8 g of yellow solids were extracted containing 90 % of the desired product.

Example 3

Reaction between 6-methyl-quinoxaline and NBS in chlorobenzene

In a 50 ml flask, 6-(Methyl)-Quinoxaline (1.25 g, 8.68 mmol) was dissolved together with N-bromosuccinimide (2.32 g, 13.0 mmol) and benzoyl peroxide (0.15 g, 0.62 mmol) in 31 g of chlorobenzene. The yellow solution was heated to 85° C. with a water bath and maintained at this temperature for two hours.

Molar concentrations and ratios are shown in the following table:

| Solvent | [6QX] | [NBS] | [BP] | [NBS]/[6QX] | [6QX]/[BP] |
|---------|-------|-------|------|-------------|------------|
| ClPh    | 0.31  | 0.46  | $2.2 \times 10^{-2}$ | 1.5 | 14 |

A sample was analyzed by GS-MS showing the following the results:

| | Reaction Time = 120 min | |
|---|---|---|
| Product | % Selectivity | % Conversion |
| 1 | 97.0 | 95.0 |
| Unknowns | 3.0 | 2.5 |

Thus, excellent selectivities and good conversions can be accomplished using chlorobenzene as solvent for the bromination of 6-methyl-quinoxaline.

Example 4

Air oxidation of 6-chloromethyl-quinoxaline to 6-quinoxaline carboxylic acid with 5% Pd/C A sample of 6-chloromethyl-quinoxaline prepared in Example 1 (1.6 g) was mixed with an alkaline solution (1.29 g of sodium hydroxide pellets dissolved in 25 g of water) to give a reddish color suspension. The catalyst was added to the aqueous suspension (0.2 g of 5% Pd/C) and the solution was refluxed with air sparging. After 48 hours, the liquid suspension was filtered to give a yellow/amber clear solution. The aqueous solution was cooled down and extracted with ether (to remove any remaining organic contaminants) followed by acidification with 1 M sulfuric acid. Upon acidification, a pale yellow solid precipitated which was filtered off, washed with water and air dried (1.0 g, ~80% yield).

The yellow powder was analyzed by infrared spectroscopy and nuclear magnetic resonance. Infrared spectroscopy showed a C=O stretching at 1708 $cm^{-1}$ which is typical for carboxylic acids, while $^1$H NMR ($d_4$-MeOH) gave the following resonances: 8.19 (d, 1H), 8.40 (dxd, 1H), 8.78 (1 H), 8.99 (2H). MS analysis showed the following fragments: 174 ($M^+$), 157 ($M^+$—OH), 129 ($M^+$—OH—CO), 103 ($M^+$—OH—CO—$C_2H_2$). The analysis is in agreement with 6-quinoxaline-carboxylic acid. The presence of the carboxylic acid was also confirmed by $ND_3$ proton exchange mass spectroscopy ($M^+$=175).

Example 5

Air oxidation of 6-bromomethyl-quinoxaline to 6-quinoxaline carboxylic acid with 5% Pd/C In a 100 ml flask, 6-methyl-quinoxaline (1.25 g, 8.68 mmol) was dissolved together with N-bromosuccinimide (2.32, 13.0 mmol) and benzoyl peroxide (0.15 g, 0.62 mml) in 31 g of chlorobenzene. The mixture was heated up to 85° C. to give a pale yellow solution that slowly turned red. The solution was maintained at 85° C. for two hours to give a red solution of 6-bromomethyl-quinoxaline. The solution was then cooled down to room temperature with the formation of a precipitate mainly composed of succinimide. The solution was then mixed with an equal volume (~31 ml) of pentane to ease the precipitation of succinimides (NHS as well as any unreacted NBS). After filtration, the orange solid obtained (1.4 g) was extracted few times with pentane (4 times, 50 ml each) to recover any remaining 6-bromomethyl-quinoxaline. The extracts were combined with the yellow solution of bromomethyl-quinoxaline and vacuum dried to give a yellow solid (1.92 g) that was suspended in an alkaline solution prepared by dissolving 2.0 g of sodium hydroxide pellets in 30 g of water. The catalyst (5% Pd/C) was added to the alkaline mixture (0.2 g) and the suspension was heated up to 85–95° C. and sparged with air for 48 hours. The black suspension was filtered to give an amber solution that was neutralized with dilute sulfuric acid to give a yellow powder (1.28 g, 85% yield) that precipitated from solution (6-quinoxaline-carboxylic acid).

Example 6

Air oxidation of 6-bromomethyl-quinoxaline to 6-quinoxaline carboxylic acid with 5% Pt/C In a 100 ml flask, 6-methyl-quinoxaline (1.25 g, 8.68 mmol) was dissolved together with N-bromosuccinimide (2.32, 13.0 mmol) and benzoyl peroxide (0.15 g, 0.62 mml) in 31 g of chlorobenzene. The mixture was heated up to 85° C. to give a pale yellow solution that turned reddish with time. The solution was maintained at 85° C. for two hours and it was then cooled down to −10° C. and filtered. The solution was vacuum dried and the orange solid residue was mixed with an alkaline solution prepared by dissolving 2.6 g of sodium hydroxide pellets in 50 ml of water. The catalyst (5% Pt/C) was added to the alkaline mixture (0.2 g) and the suspension was heated up to 85–95° C. with air sparging.

Analysis showed that the reaction was finished after sparging the solution with air for 10 hours. The aqueous solution was cooled down to room temperature and filtered. The yellow solution obtained was neutralized with 3.18 g of 96% sulfuric acid dissolved in 5 ml of water. A yellow precipitated was formed during the addition of acid. The yellow precipitate was filtered and air dried to give 0.67 g of dry product (45% yield).

The lower yield in this experiment is probably attributed to the fact that the precipitate of succinimides formed after cooling the chlorobenzene solution of bromomethyl-quinoxaline was not washed with pentane. Thus, some bromomethyl-quinoxaline was probably lost in that step. Therefore, the procedure used in Example 2 and 5 are recommended to get better yields. This example illustrates that 5% Pt/C can also be employed to oxidize the 6-bromomethyl-quinoxaline to the carboxylic acid.

Example 7

Preparation of a chlorobenzene solution of 6-bromomethyl-quinoxaline

In a 50 ml flask, 6-methyl-quinoxaline (1.25 g, 8.68 mmol) was dissolved together with N-bromosuccinimide (2.32 g, 13.0 mmol) and benzoyl peroxide (0.15 g, 0.62 mmol) in 31 g of chlorobenzene. The solution was stirred and heated to 85° C. for 2.0 hours and the reaction mixture was analyzed by GCMS. The molar concentrations and molar ratios of the reactants are shown in the following table:

| Solvent | [6QX] | [NBS] | [BP] | [NBS]/[6QX] | [6QX]/[BP] |
|---|---|---|---|---|---|
| ClPh | 0.31 | 0.46 | $2.2 \times 10^{-2}$ | 1.5 | 14 |

The results are summarized in the following tables:

| | Reaction Time = 120 min | |
|---|---|---|
| Product | % Selectivity | % Conversion |
| 1 | 97.0 | 94.0 |
| 2 | 2.1 | 2.7 |
| unknowns | 2.9 | 2.0 |

The chlorobenzene solution was cooled down to room temperature and one volume of pentane (31 ml) was added to aid the precipitation of succinimides. The orange solid was filtered, washed with pentane and air dried (1.20 g). The pentane was removed under vacuum to give a clear yellow solution of 6-bromomethyl-quinoxaline.

Example 8

Air oxidation of a chlorobenzene solution of 6-bromomethyl-quinoxaline to 6-quinoxaline carboxylic acid with 5% Pd/C The solution obtained in Example 7 was mixed with aqueous alkali prepared by dissolving 3.0 g of sodium hydroxide pellets in 30 ml of water. A phase transfer catalyst was added (0.1 g tetra-n butyl ammonium chloride) to improve the partition coefficient of the base in the organic phase. The mixture was heated to reflux for few minutes and the catalyst (0.2 g 5% Pd/C) was added. Air was sparged through the mixture for a few hours and the chlorobenzene that escaped from the reaction vessel was condensed in a cooled trap. After 24 hours, most of the chlorobenzene was removed by the flow of air leaving the aqueous phase inside the flask. At this point, the reaction mixture was visually inspected showing that the supported catalyst agglutinated possibly due to the presence of too many organic bodies in the aqueous phase. The agglutination of the supported catalyst made the oxidation method very ineffective probably due to surface area loss. This catalyst was filtered from the reaction mixture followed by the addition of more fresh catalyst (0.2 g). The oxidation was continued for a total reaction time of 72 hours. The catalyst was filtered and the aqueous phase was acidified with a mineral acid (3.6 g of 96% sulfuric acid dissolved in 10 ml of water). No yellow precipitate of 6-quinoxaline-carboxylic acid was formed during the addition of acid. Its precipitation was probably prevented by the presence of chloroaromatics remaining in the aqueous phase. The yellow solution was then extracted with ether (5 times, 100 ml each) to give a yellow solid (0.57 g) that presumably contained 6-quinoxaline-carboxylic acid. The sample was analyzed by $^1$H NMR (CD$_3$OD) and showed a very complex spectrum clearly indicating that the sample produced was not of the same quality as the one described in Example 4. Nevertheless, the resonances corresponding to 6-quinoxaline-carboxylic acid were clearly observed. Thus, this procedure was ineffective in providing a good sample of 6-quinoxaline-carboxylic.

Throughout this application, various publications have been referenced. The disclosures in these publications are incorporated herein by reference in order to more fully describe the state of the art.

1. R. Granger, S. Deadwyler, M. Davis, B. Moskovitz, M. Kessler, G. Rogers, G. Lynch, *Synapse*, 22, pp. 332–337, 1996; and (b) G. Lynch, M. Kessler, G. Rogers, J. Ambross-Ingerson, R. Granger, R. S. Schehr, *International Clinical Psychopharmacology*, 11, pp. 13–19, 1996.

2. (a) J. Gum, *J. Org. Chem.*, 30, 3982, 1965; (b) W. H. Huang, A. R. Lee, C. I. Lin, M. H. Yen, *Yixue Yanjiu*, 13, 247–54, 1993.
3. B. Schilling, *Ber.*, 34, pp. 902–907, 1901.
4. (a) A. Tallec, *Ann. Chim. (Paris)*, 3, 164, 1968; (b) V. Cere, D. Dal Monte, E. Sardi, *Tetrahedron*, 28, 3271, 1972.
5. M. Hudlicky "*Oxidations in Organic Chemistry*", ACS Monograph 186, 1990.
6. R. A. Sheldon, J. K. Kochi, "*Metal-Catalyzed Oxidation of Organic Compounds*", Chapter 5, pp. 121–151, Academic Press, 1981.
7. 2,3-Pyrazinedicarboxylic acid: "*Organic Synthesis*" Coll. Vol. 4 pp. 824–827, J. Wiley & Sons, Inc. NY, 1963.
8. R. A. Sheldon, J. K. Kochi, "*Metal-Catalyzed Oxidation of Organic Compounds*", Chapter 7, pp. 189–214, Academic Press, 1981.
9. J. C. Cavagnol, F. Y. Wiselogle, *J. Am. Chem. Soc.*, 69, 795, 1947.
10. Thomas D. Waugh, *NBS: N-Bromosuccinimide Its Reactions and Uses;* Arapahoe Chemicals, Inc. Boulder Co. 1951.
11. D. F. Gavin, U.S. Pat. No. 3,690,963 (1976).
12. Benzoyl Piperidine: "*Organic Synthesis*", Coll. Vol. 1 pp. 108–110, J. Wiley & Sons, Inc. New York, 1943.

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

What is claimed is:

1. A method for preparing quinoxaline-5- and 6-carboxylic acids (I) which comprises contacting an aqueous alkaline suspension of a 5- or 6-halomethyl quinoxaline (II) with oxygen in the presence of a transition metal catalyst, to form the respective quinoxaline-5- or 6-carboxylic acid (I), wherein X is halogen

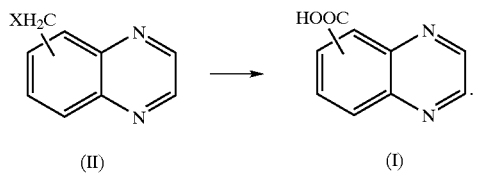

2. The method according to claim 1, wherein the quinoxaline-5- or 6-carboxylic acid is a quinoxaline-5-carboxylic acid (I).

3. The method according to claim 1, wherein the quinoxaline-5- or 6-carboxylic acid is a quinoxaline-6-carboxylic acid (I).

4. The method according to claim 1, wherein the aqueous alkaline suspension of a 5- or 6-halomethyl quinoxaline (II) has a pH value in the range from about 8 to about 14.

5. The method according to claim 1, wherein the transition metal catalyst is selected from the group consisting of Pd, Pt, Ru, Co, Mn, Cu, and V.

6. The method according to claim 5, wherein the transition metal catalyst is Pd/C or Pt/C.

* * * * *